United States Patent [19]
Firoozabady et al.

[11] Patent Number: 5,589,613
[45] Date of Patent: Dec. 31, 1996

[54] CARNATION PLANTS AND METHODS FOR THEIR TRANSFORMATION AND PROPAGATION

[75] Inventors: Ebrahim Firoozabady, Pleasant Hill, Calif.; Christine Lemieux, Boulder, Colo.; Benjamin A. Moll, Berkeley; Karol Robinson, Moraga, both of Calif.

[73] Assignee: Florigene Europe B.V., Rijnsburg, Netherlands

[21] Appl. No.: 150,528

[22] Filed: Nov. 10, 1993

Related U.S. Application Data

[63] Continuation of Ser. No. 678,915, Apr. 1, 1991, abandoned.

[51] Int. Cl.$^6$ ........................................... A01H 4/00
[52] U.S. Cl. ..................... 800/205; 800/DIG. 10; 435/240.4; 435/240.49; 435/240.48; 435/172.3
[58] Field of Search ............................ 435/240.4, 240.45, 435/240.48, 240.49, 172.3; 800/205, DIG. 10

[56] References Cited

PUBLICATIONS

Woodson (1989) Hort. Science 24:80 (Abstract No. 172).
Petru et al. (1974) Biologia Plantarum 16:450–453.
Lesham (1986) Hort. Science 21:320–321.
Frey et al. (1989) Hort. Science 24:74 (Abstract No. 124).
Hackett et al. (1987) Amer. Soc. Hort. Sci. 90:365–369.
Earle et al. (1975) Hort. Science 10:608–610.
Davis et al. (1977) J. Amer. Soc. Hort. Sci. 102:48–53.
Ziv et al. (1983) Plant Cell Tissue Organ Culture 2:55–65.
Miller et al. (1991) Annals of Botany 67:35–42.
Winans et al. (1986) Proc. Natl. Acad. Sci. USA 83:8278–8282.
Horsch et al. (1985) Science 227:1229–1231.
Frey and Janick (1991) J. Amer. Soc. Hort. Sci. 116:1108–1112.
Leskem (Apr. 1986) Hortscience 21(2):320–321.
Winans, et al. (Nov. 1986) Proc. Natl. Acad Sci, USA 83:8278–8282.
Horsch, et al. (8 Mar. 1985) Science 227:1229–1231.
Hackett, et al (1987) Amer. Soc. Hort. Sci. 90:365–369.
Woodson, et al (1989) Hort. Science 24:80 (Abstract No. 172).
Frey, et al (1991) J. Amer. Soc. Hort. Sci 116:1108–1112.
Fiola, et al (1990) Plant Cell, Tissue and Organ Culture 20:223–228.

*Primary Examiner*—Che S. Chereskin
*Attorney, Agent, or Firm*—Townsend and Townsend and Crew LLP

[57] ABSTRACT

Carnation plant material is transformed by cocultivation with Agrobacterium cells carrying an exogenous DNA sequence. In particular, by initiating callus formation on the plant material, transformed shoots may be produced in a suitable medium. Plantlets may be produced from the shoots by initiating root formation and subsequently transferring the rooted shoots to soil.

41 Claims, 3 Drawing Sheets

CARNATION PLANTS AND METHODS FOR THEIR TRANSFORMATION AND PROPAGATION

This is a continuation of application Ser. No. 07/678,915 filed Apr. 1, 1991, now abandoned.

BACKGROUND OF THE INVENTION

1. Field of the Invention

The present invention relates generally to methods for culturing and genetically altering higher plants. More particularly, the present invention relates to methods for culturing and genetically transforming tissue material from carnation plants.

The carnation, *Dianthus caryophyllus*, is a popular ornamental plant and highly valued for its cut flowers. As with many ornamental plant species, breeders have long sought to improve existing varieties and to create new cultivars using conventional techniques, such as cross-breeding and somatic clonal variation. Phenotypic variations of particular interest include color, fragrance, morphology, herbicide resistance, pesticide resistance, environmental tolerance, vase life of the cut flower, and the like. While improvements and variations in many or all of these characteristics have been achieved, progress is slow because of the inherently random nature of such breeding approaches. Indeed, the introduction of any particular characteristic requires a substantial effort if it can be achieved at all.

The propagation of carnation plants through the regeneration of plant parts and callus, as well as through micropropagation of shoot cultures, can be difficult even when it is not desired to introduce genetic alterations. In particular, methods proposed for the regeneration of carnation tissue often result in "vitrified" shoots having a glassy or translucent appearance and an abnormal morphology. Moreover, conventional regeneration methods often have regeneration frequencies below about 10% Micropropagation methods often are slow and produce few shoots per original cultured shoot. Those methods involving liquid medium cultures can be laborious and care subject to contamination.

For these reasons, it would be desirable to provide improved regeneration and micropropagation procedures for the efficient in vitro reproduction of carnation plant material. It would be particularly desirable to combine recombinant DNA technology with the regeneration and micropropagation techniques in order to produce new carnation cultivars in a controlled and predictable manner. Such recombinant DNA methods should provide for transformation, should be capable of introducing preselected exogenous gene(s) to the carnation plant, and should permit selection of transformed plant materials which are capable of expressing the exogenous gene(s). The method should also produce regenerated carnation plants which have stably incorporated the desired exogenous DNA sequences.

2. Description of the Background Art

Woodson (1989) Hort. Science 24:80 (Abstract No. 172) briefly describes the use of *Agrobacterium tumefaciens* to transform carnation petal explants. While the regeneration of roots in putative transformants is asserted, no regeneration of whole plants is described. The regeneration of carnation plants (without transformation) from tissue has been described. See, e.g., Petru et al. (1974) Biologia Plantarum 16:450–453 (stem formation in callus from hypocotyl and apical meristems); Lesham (1986) Hort. Science 21:320–321 (regeneration from callus and petals); and Frey et al. (1989) Hort. Science 24:74 (Abstract No. 124) (regeneration from petals and other explants with a callus stage; 1.5–3% of shoots survived transfer to soil). The micropropagation (shoot multiplication) of cultured shoots and meristem material has been described. See, e.g., Hackett et al. (1987) Amer. Soc. Hort. Sci. 90:365–369 (shoot tip propagation); Earle et al. (1975) Hort. Science 10:608–610 (shoot tip propagation); Davis et al. (1977) J. Amer. Soc. Hort. Sci. 102:48–53 (shoot tip propagation); and Ziv et al. (1983) Plant Cell Tissue Organ Culture 2:55–65 (describes vitrification in shoot tip culture).

SUMMARY OF THE INVENTION

The present invention comprises methods for genetically transforming carnation plant material, particularly leaf and petal explants, by cocultivating (or otherwise inoculating) the plant material with Agrobacterium cells carrying an exogenous DNA sequence. After cocultivation, callus formation is preferably initiated in the plant material. Transformed plant material (calli or shoots) is selected, typically by exposure to a plant selection agent which inhibits formation of plant material which does not express the exogenous DNA sequence. In the preferred embodiments, plantlets are produced from the selected (transformed) plant material by first regenerating transformed shoots and then inducing root formation in the regenerated transformed shoots.

The present invention further comprises carnation callus material and carnation plants which incorporate such exogenous DNA sequences. Preferably, such transformed calli and plants are obtained by the methods of the present invention.

The methods of the present invention provide a particularly convenient technique for selectively breeding new carnation cultivars in a predictable and expeditious manner. A variety of traits, such as color, fragrance, herbicide resistance, insect resistance pesticide resistance, flower vase life, environmental tolerance, disease resistance, horticultural traits, and the like, may be introduced into the carnation explant material by stably incorporating appropriate genes into the chromosomes of the selected plant cells, which may then be regenerated into carnation plants.

It has been found that use of a transformation method which involves passage of at least some of the cocultivated transformed plant material through the callus stage has certain advantages. This approach appears to reduce or eliminate chimerism, i.e., the presence of both transformed and non-transformed cells, in the regenerated shoot and rooted plant materials. Such chimerism can be a problem when the transformed explant material is directly regenerated without passage of any of the plant material through the callus stage. A preferred embodiment involves selection of initial transformants during the callus stage using a selection agent which is present at levels which inhibit (but do not kill) the non-transformed calli; this has been found to provide for high proliferation levels of transformed plant material. Such high proliferation levels greatly facilitate screening for individual calli and plants which have successfully incorporated a desired phenotype.

| Lanes | |
|---|---|
| 1–5 | Samples from transgenic plants of Example 1. |
| 6–7 | Samples from transgenic plants of Example 2. |
| 8 | Sample from transgenic plants of Example 1. |
| 9, 11 | Samples from nontransformed control of Example 1. |
| 12 | Sample from nontransformed control of Example 2. |
| 10 | Sample from spiked-plasmid DNA in control tissues (used as positive control). |
| 13, 14 | Samples from reactions in the absence of sample DNA (negative controls). |

Figure 3:
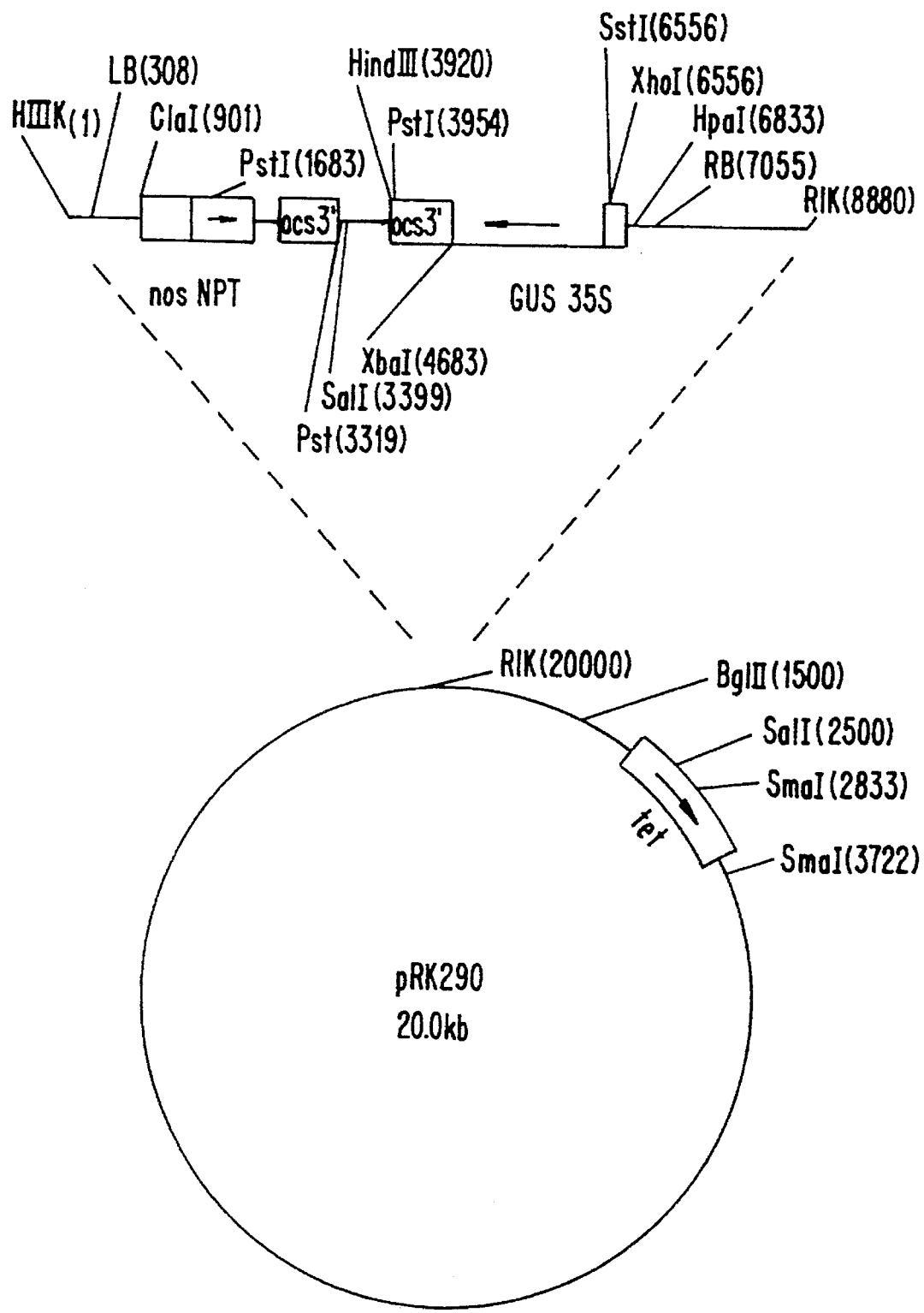

FIG. 3 is a map of binary plasmid pJJ3499 employed in Example 2. The construction of pJJ3499 is the same as pSLJ1911 synthase except that the nopaline synthase promoter controls the NPT gene.

DESCRIPTION OF THE SPECIFIC EMBODIMENTS

According to the present invention, genetically transformed carnation plants and calli are obtained by the selective introduction of exogenous DNA sequence(s) into the chromosomes of cultured carnation plant tissue material. The plant tissue material will be somatic tissue from any source that is capable of producing calli, such as leaf explants, petal explants, stamen filaments, stem sections, shoot tips, receptacles, sepals, and the like, with leaf explants and petals being preferred. The use of leaf explants is particularly preferred.

Any variety of carnation plant (*Dianthus caryophyllus*) may be used as a source of the plant tissue material. Suitable varieties include the "Sim type" which is available in a number of colors including red, white, pink, orange, and variegated forms; various Mediterranean types; and miniature types. Of particular interest are certain Sim varieties, including William Sim, Improved White Sim, Nathalie, Manon, Tibet, Cephali, Iceland, Cerise Royalette and Sandra.

Leaf explant material may be obtained from whole plant or plantlet but is preferably obtained from carnation shoots produced in tissue culture by conventional techniques. Such conventional techniques are described in the scientific literature, see, for example, Mii et al., in *Handbook of Cell Culture*, Vol. 5, Ammirato et al., eds., Vol. 5, McGraw-Hill Publishing Company, New York, 1990, and Besemer, *Introduction to Floriculture*, Larsen, ed., Chapter 2, Academic Press, Inc., 1980, the disclosures of which are incorporated herein by reference.

A suitable technique for preparing a carnation shoot culture begins with meristem tissue from the node (i.e., the slightly enlarged portion of the stem where leaves and bud arise and where branches originate) or in the shoot tip or apex (i.e., the portion of the shoot containing apical or primary meristem). The meristem material is surface sterilized, for example with 75% ethanol for two minutes followed by 20% commercial bleach (sodium hypochlorite) with 0.1% Tween®-20 for 20 minutes, followed by rinsing several times with distilled or deionized water. The sterilized meristem tissue is then divided into pieces from about 1 to 3 mm in size.

Preferably, the meristem tissue is cultured in a shoot multiplication medium containing nutrients, an energy source, an auxin, and a cytokinin, with benzyladenine (BA) being the preferred cytokinin and naphthalene acetic acid (NAA) being the preferred auxin. The BA is present at from about 0.5 to 5 mg/l preferably at about 1 mg/l and the NAA is present at from about 0.005 to 1 mg/l preferably at about 0.02 mg/l. A preferred multiplication medium is BN medium described in the Experimental section hereinafter. Using this medium, a large number of shoots, typically from about 20 to 50, may be obtained from a single meristem culture within from about 6 to 8 weeks. Additional shoots, usually from about 50 to 100, can be obtained by subculturing the first generation of shoots.

Prior to obtaining the leaf explant material, it is desirable to subculture the first or subsequent generation shoots on a medium containing nutrients and an energy source but free from growth regulators in order to reduce the level of multiplication and enhance subsequent callus formation, as described in more detail hereinafter. A suitable pretreatment medium is MSO medium, as set forth in the Experimental section hereinafter.

Transformation efficiency of the leaf explant material may be improved by subjecting the cultured shoots to a heat shock treatment, usually heating the culture medium to a temperature from about 35° C. to 45° C., preferably to about 40° C., for a time period from about 2 to 8 hours, preferably about 4 hours.

The shoots are allowed to grow until they are from about 1 to 5 cm in length, preferably being from about 2 to 3 cm in length, and contain from about 5 to 10 leaves. The leaves are then cut or pulled from the individual shoots, with leaves which are about 5 to 15 mm in size being preferred. Shoot primordia on the base of the leaf are preferably removed, typically using forceps, in order to eliminate preformed meristems, increase callus formation, and induce wound sites to enhance subsequent infection by Agrobacterium cells. The shoot primordia are then discarded. The leaf base, the lower 5 to 10 mm portion of the leaf, is preferably used and obtained by cutting off the leaf tip.

The petal explant material is obtained from the flower buds of established carnation plants. Preferably, the flower buds are obtained when not yet opened and are harvested from plants grown in a greenhouse. The buds are preferably from about 1 to 3 cm in length and are surface sterilized, typically using the technique described above for leaf explant material. The basal portions of the petals are typically about 5 mm in length, and are isolated for culturing.

The petal explant material prepared as just described may be used immediately or may be stored under refrigeration, typically at 2° C. to 5° C., for up to about two weeks before use in cocultivation as described hereinafter.

The exogenous DNA sequences to be introduced will usually carry at least one selectable marker gene to permit selection of transformed plant material (i.e., those cells which have incorporated the exogenous DNA into their chromosomes), as well as one or more "functional" genes which are chosen to provide, enhance, suppress, or otherwise modify expression of a desired trait or phenotype in the resulting plant. Such traits include color, fragrance, herbicide resistance, pesticide resistance, disease resistance, insect resistance environmental tolerance, morphology, growth characteristics, and the like. A screenable marker is preferably also present.

The functional gene(s) to be introduced may be a structural gene which encodes a polypeptide which imparts the desired phenotype. Alternatively, the functional gene may be a regulatory gene which might play a role in transcriptional and/or translational control to suppress, enhance, or otherwise modify the transcription and/or expression of an endogenous gene within the carnation plant. It will be appreciated that control of gene expression can have a direct impact on the observable plant characteristics. Other functional "genes" include sense and anti-sense DNA sequences which may be prepared to suppress or otherwise modify the expression of endogenous genes. The use of anti-sense is described generally in Van der Kroll, et al., *Nature* (1988) 333:866–869, the disclosure of which is incorporated herein by reference. The use of sense DNA sequences is described in various references, including Napoli et al. (1990) Plant Cell, 2:279–289 and van der Krol et al. (1990) Plant Cell, 2:291–299, the disclosures of which are incorporated herein by reference.

Structural and regulatory genes to be inserted may be obtained from depositories, such as the American Type Culture Collection, Rockville, Md. 20852, as well as by isolation from other organisms, typically by the screening of genomic or cDNA libraries using conventional hybridization techniques, such as those described in Maniatis et al., *Molecular Cloning*—A Laboratory Manual, Cold Spring Harbor Laboratory, Cold Spring Harbor, N.Y. (1985). Screening may be performed by (1) nucleic acid hybridization using homologous genes from other organisms, (2) probes synthetically produced to hybridize to particular sequences coding for desired protein sequences, or (3) DNA sequencing and comparison to known sequences. Sequences for specific genes may be found in various computer databases, including GenBank, National Institutes of Health, as well as the database maintained by the United States Patent Office.

The genes of interest may also be identified by antibody screening of expression libraries with antibodies made against homologous proteins to identify genes encoding for homologous functions. Transposon tagging can also be used to aid the isolation of a desired gene. Transposon tagging typically involves mutation of the target gene. The mutated gene is isolated in which a transposon has inserted into the target gene and altered the resulting phenotype. Using a probe for the transposon, the mutated gene can be isolated. Then, using the DNA adjacent to the transposon in the mutated gene as a probe, the normal wild-type allele of the target gene can be isolated. Such techniques are taught, for example, in McLaughlin and Walbot (1987) Genetics, 117:771–776; Dooner et al. (1985) Mol. Gen. Genetics, 200:240–246; and Federoff et al. (1984) Proc. Natl. Acad. Sci. USA, 81:3825–3829, the disclosures of which are incorporated herein by reference.

Particular genes which may be incorporated into carnation callus cells according to the method of the present invention include rolC (morphology); Acc synthase (senescence control); Hf1 and Ht1 (color modification); Bt genes or protease inhibitors (insect tolerance); chalcone synthase genes (color modification using sense approach).

The selectable marker gene on the DNA sequences to be inserted will usually encode a function which permits the survival of transformed plant material in a selective medium, e.g., a callus initiation medium as described hereinafter. Usually, the selectable marker gene will encode antibiotic resistance, particularly kanamycin resistance and geneticin (G418) resistance; herbicide resistance, e.g., chlorsulfuron resistance; or the like. The composition of a suitable selective medium is described hereinbelow.

In addition to the "functional" gene and the selectable marker gene, the DNA sequences may also contain a screenable marker, e.g., reporter gene, which facilitates screening of the transformed plant material for the presence and expression of the exogenous DNA sequences. Exemplary reporter genes include β-glucuronidase and luciferase, as described in more detail hereinafter.

The exogenous DNA sequences will be introduced to the carnation plant material by cocultivation (incubation in vitro or in vivo) with Agrobacterium cells which carry the sequences to be transferred within a transfer DNA (T-DNA) region found on a suitable plasmid, typically the Ti plasmid. Ti plasmids contain two regions essential for the transformation of plant cells. One of these, the T-DNA region, is transferred to the plant nuclei and induces tumor formation. The other, referred to as the virulence (vir) region, is essential for the transfer of the T-DNA but is not itself transferred. By inserting the DNA sequence to be transferred into the T-DNA region, introduction of the DNA sequences to the plant genome can be effected. Usually, the Ti plasmid will be modified to delete or inactivate the tumor-causing genes so that they are suitable for use as vector for the transfer of the gene constructs of the present invention. Other plasmids may be utilized in conjunction with Agrobacterium for transferring the DNA sequences of the present invention to plant cells, as known in the art.

The construction of recombinant Ti and pTAR plasmids may be accomplished using conventional recombinant DNA techniques, such as those described in Maniatis et al., supra. Frequently, the plasmids will include additional sequences and selective marker genes which permit manipulation and construction of the plasmid in suitable hosts, typically bacterial hosts other than Agrobacterium, such as *E. coli*.

The genes within the DNA sequences will typically be linked to appropriate transcriptional and translational control sequences which are suitable for the carnation plant host. For example, the gene will typically be situated at a distance from a promoter corresponding to the distance at which the promoter is normally effective in order to ensure transcriptional activity. Usually, a polyadenylation site and transcription termination sites will be provided at the 3'-end of the gene coding sequence. Frequently, the necessary control functions can be obtained together with the structural gene when it is isolated from a target plant of other host. Such intact genes will usually include coding sequences, intron(s), a promoter, enhancers, and all other regulatory elements either upstream (5') or downstream (3') of the coding sequences.

Optionally, a binary vector system present in Agrobacterium may be used to introduce the DNA sequences according to the present invention. A first plasmid carries the T-DNA while a second plasmid carries a virulence (vir) region. By incubating such an Agrobacterium strain with the plant cells, infection of the plant cells can be achieved. Hoekema, et al., *Nature* (1983) 303:179–180.

Suitable Agrobacterium strains include *Agrobacterium tumefaciens* and *Agrobacterium rhizogenes*. While the wild-type *Agrobacterium rhizogenes* may be used, the *Agrobacterium tumefaciens* should be "disarmed," i.e., have its tumor-inducing activity removed, prior to use. Preferred *Agrobacterium tumefaciens* strains include LBA4404, as described by Hoekema et al. (1983) *Nature*, 303:179–180, and EHA101 Hood, et al., (1986) J. Bacteriol., 168:1291–1301. A preferred *Agrobacterium rhizogenes* strain is 15834, as described by Birot et al. (1987) Plant Physiol. Biochem., 25:323–325.

After the Agrobacterium strain(s) carrying the desired exogenous DNA sequence(s) have been prepared, they will usually be cultured for a period of time, prior to incubation with the carnation plant material. Initially, the Agrobacterium may be cultured on a medium, preferably solid, including nutrients, an energy source, and a gelling agent. Suitable nutrients may include salts, tryptone, and yeast extracts, while most sugars are suitable as the energy source and the gelling agent can be agar, Gel-rite®, or the like. A preferred medium is L-Broth. Usually, medium will include an antibiotic to select for Agrobacterium carrying the DNA sequences.

The Agrobacterium cells are typically cultured for about one to three days, preferably in the dark at about 28° C., and are collected while still a white-cream color, i.e., before browning, typically by being scraped off the solid medium. The cells are then suspended in a liquid medium, e.g., liquid L-broth, or more preferably in an induction broth containing the following components in the ranges shown or at the approximate preferred levels shown:

|  | Broad Range | Preferred |
|---|---|---|
| Ammonium chloride | 0.5–3 g/l | 1 g/l |
| Magnesium sulfate | 0.5–3 g/l | 1 g/l |
| Potassium chloride | 0.05–2 g/l | 0.15 g/l |
| Calcium | 2–20 mg/l | 10 mg/l |
| Ferrus sulfate | 0.5–10 mg/l | 2.5 mg/l |
| Phosphate monobasic | 50–1000 mg/l | 272 mg/l |
| MES | 1000–10,000 mg/l | 3904 mg/l |
| Sucrose | 10–30 g/l | 20 g/l |
| Glucose | 2–30 g/l | 5 g/l |
| Acetosyringone | 10–200 μM | 100 μM |
| pH | 5–7 | 5–6 |

The Agrobacterium cells are cultured in the L-broth or induction broth for about one to ten hours, while being agitated, preferably at moderate temperatures from about 20° C. to 30° C.

The exogenous DNA sequences are transferred to the carnation plant material by inoculation and cocultivation with the Agrobacterium cells which carry the sequences of interest. The cocultivation is carried out in a suitable cocultivation medium comprising a general growth medium including nutrients, an energy source, and growth regulating hormones present in amounts effective to promote survival and growth of the carnation plant cells. In addition to the general growth medium, the cocultivation medium may include an induction compound which is selected to induce the virulence (vir) region of Agrobacterium to enhance transformation efficiency. The induction compound can be any phenolic compound which is known to induce such virulence, preferably being acetosyringone (AS) present at from about 10 to 200 μM.

The general growth medium should include an adequate supply of both inorganic and organic nutrients, including nitrogen and salts. A variety of basal nutrient medium are known which provide adequate supplies to support plant cell growth, such as MS (Murashige et al. (1962) Physiol. Plant 15:473–479), White's (White, A Handbook of Plant Tissue Culture, Jaques Cattell Press, Lancaster, Pa., 1943), B5 (Gamborg et al. (1968) Exp. Cell Res. 50:151–158), N6 (Chiu et al. (1975) Sientia Sinica 18:659–668), and the like. Any sugar may be employed as the energy source. Among the appropriate choices are glucose, maltose, sucrose, lactose, fructose, or sucrose in combination with any of the above sugars. A preferred sugar for this purpose is sucrose, at from about 10 to 50 g/l, but molar equivalents of other sugars may also be employed. The MS medium described in Murashige et al. (1962), supra., contains an appropriate level of sugar. Other energy sources, such as acetate, may also be employed.

The growth hormones included in the general growth medium will include at least one auxin and at least one cytokinin. The auxins may be any auxin, natural or synthetic, for example, indole acetic acid (IAA), naphthalene acetic acid (NAA), (2,4-dichlorophenoxy) acetic acid (2,4-D), picloram and dicamba. The cytokinin may be selected from any of the known cytokinins, natural or synthetic, for example thidiazuron (TDZ), 6-benzyladenine (6-BA), zeatin (ZEA), kinetin (KIN), and isopentyladenosine (iP). Callus may be induced in the presence of several combinations of auxin and cytokinin. However, superior results are observed on an induction medium comprising 2,4-D and 6-BA. An alternate useful combination is NAA with kinetin. Generally, an auxin will be present in an amount of about 0.1 to 10 mg/ml, and cytokinin in an amount of about 0.2 to 15.0 mg/ml. When the auxin is NAA, the concentration in the medium is preferably from about 0.05 to 2.5 mg/l, and most preferably about 0.2 mg/l. When 2,4-D is used, the amount is preferably from about 0.05 to 5.0 mg/l and most preferably about 5.0 mg/l. When the cytokinin is kinetin, the concentration in the medium is preferably from about 0.5 to 5.0 mg/l and most preferably about 0.5 mg/l. When zeatin is used, the concentration is preferably from about 0.2 to 12.5 mg/l and most preferably about 1.5 mg/l.

Those skilled in the art will recognize that other components which are frequently employed in plant tissue culture may be incorporated in the general growth medium. Addition of various vitamins, e.g., MS vitamins, White vitamins, nicotinic acid, inositol, pyridoxine or thiamine is common. Similarly, for solid media, an appropriate amount of solidifying agent, such as agar or Gel-rite®, is also added to the mixture.

The carnation explant material prepared as described above is mixed with a suspension of the Agrobacterium cells in the cocultivation medium, with the cells present at at least about $10^7$ cells/ml, preferably being at least about $10^8$ cells/ml, and more preferably being about $10^9$ cells/ml. The Agrobacterium suspension will normally be applied over a plurality of the explants in the suitable container, such as petri dishes. The mixture is preferably shaken for an extended period, typically from 1 to 10 hours, preferably from 2 to 3 hours, usually at room temperature. The mixture is then placed on a solid phase matrix, such as filter paper, saturated with the cocultivation medium. The cocultivation continues on the filter paper at room temperature for a number of days, usually from about 3 to 6 days, with the culture being exposed to light for a portion of each 24 hour period.

In the cocultivation medium, for leaf explant material, 6-BA is the preferred cytokinin, and 2,4-D is the preferred auxin, each preferably present at about 0.5 mg/l in the cocultivation medium. An exemplary cocultivation medium for leaf is BDAS, as described in the Experimental section hereinafter. For petal explants, thidiazuron (TDZ) is the preferred cytokinin, preferably present at about 1 μM in the cocultivation medium. An exemplary cocultivation medium for petal is DTAS, as described in the Experimental section hereinafter.

At the end of the cocultivation period, the Agrobacterium cells will have grown so that colonies are visible on the explant material in contact with the medium. Optionally, feeder cell layers (as described in Horsch and Jones (1980) In Vitro 16:103–106, the disclosure of which is incorporated herein by reference) may enhance transformation efficiencies by recovering the transformed cells attached by Agrobacterium during cocultivation.

After the cocultivation has been completed, the explant material is transferred to a callus initiation medium containing nutrients, an energy source, and auxin, and a cytokinin, generally as described above for the general growth medium. In addition, the callus initiation medium will include a plant selection agent which will inhibit growth and proliferation of plant material which has not been transformed, and in particular, plant material which does not express the selectable marker gene introduced as a part of the exogenous DNA sequences. The callus initiation medium will further include an anti-Agrobacterium antibiotic to inhibit the growth of any Agrobacterium cells which may have been introduced into the callus initiation medium.

The particular plant selection agent will depend, of course, on the nature of the selectable marker gene. Usually, the selectable marker gene will encode antibiotic resistance and the plant selection agent will be the particular antibiotic substance for which resistance has been encoded in the transformed explants. For example, if the selectable marker gene is NPT II which encodes kanamycin-geneticin resistance, the selection agent should be either geneticin, e.g., G418, or kanamycin. For the chlorsulfuron resistance gene, the plant selection agent will be chlorsulfuron. Preferably, the plant selection agent will be present in the callus initiation medium at a "sublethal" concentration where the non-transformed plant material is inhibited from proliferating but remains viable, i.e., it is not killed. For geneticin, such a concentration is generally in the range from about 20 to 75 mg/l, for kanamycin, the concentration is generally in the range from about 200 to 300 mg/l, and for chlorsulfuron, the concentration is generally in the range from about 2 to 25 µg/l. It has been found that the use of such sublethal concentrations of the selection agent effectively limits callus formation from non-transformed cells, while permitting very high levels of callus formation from the transformed cells. The use of lethal levels of the selection agent, in contrast, typically diminishes callus production even in the transformed plant cells. Thus, the use of sublethal selection agent levels provides a much more efficient and productive process.

An alternative selection approach calls for use of selective agents (e.g., kanamycin) sprayed on the plant materials, in addition to having the selection agent in the medium. Spray can start as soon as seven days after cocultivation and continues with 3–10 day intervals until completely transformed shoots are obtained. Spray can be done with different selection agents (see above). Concentrations of the agents should be increased 5–15 times relative to what is used in the medium, due to the short time exposure of plant materials to the agents.

Suitable anti-Agrobacterium antibiotics include carbenicillin, typically present at from about 200 to 1000 mg/l, vancomycin, typically present at from about 100 to 500 mg/l, cloxacillin, typically present at from about 200 to 1000 mg/l, cefotaxin, typically present at from about 200 to 1000 mg/l, erythromycin, typically present at from about 200 to 1000 mg/l, and the like.

For callus initiation of leaf explants, a preferred medium is BDC, as described in the Experimental section hereinafter, supplemented with benzyladenine at about 0.5 mg/l and 2,4-D at about 0.5 mg/l. The selection agent can be any of those set forth above. For petal explants, the preferred medium is DTC, as set forth in the Experimental section hereinafter, supplemented with the appropriate selection agent.

The explant materials are maintained in the callus initiation medium in a growth chamber under controlled conditions of light and temperature. For example, light exposure of 16 hours per day at about 1500 to 3000 lux at a temperature of about 24° C. has been found to produce calli after about 2 to 3 weeks. With lethal levels of plant selection agent, about 2 to 5% of the explants will usually produce calli on a surface while with sublethal levels of selection agent, the percentage of explants which produce calli can increase up to about 50%.

The culture period on callus initiation medium, as described above, may be reduced, e.g., to four days or less. Alternatively, the callus initiation stage may be eliminated, with explants transferred directly onto regeneration medium (see below) after cocultivation. Using this approach, shoots may be directly regenerated from the explants (although nontransferred calli may still form). Under these conditions the frequency of shoot regeneration and callus production on regeneration medium can be as high as 100% and 50%, respectively, in the absence of plant selection agent, and 2–5% for each in the presence of lethal levels of selection agents. Even, however, where the callus initiation stage is used, transformed shoots may result from noncallus cells (in addition to, or instead of, resulting from transformed calli).

The explants having established calli on their surface are next transferred to a regeneration medium in order to induce shoot formation. The regeneration medium contains nutrients, an energy source, an auxin, and a cytokinin, generally of the type and in the amounts set forth for the general growth medium described above. For the regeneration medium, the preferred auxin is indole butyric acid (IBA) present at from about 1 to 5 µM, most preferably at about 2.5 µM, and the preferred cytokinin is thidauzuron present at about 0.5 to 2 µM, most preferably at about 0.75 µM. A solidifying agent, such as Gel-rite® is added, and the medium further contains the plant selection agent and the anti-Agrobacterium antibiotic, normally the same ones that were used in the callus initiation medium. A preferred regeneration medium for leaf is ITC, as described in the Experimental section hereinafter, containing 500 mg/l carbenicillin and the appropriate plant selection agent.

For petal, the regeneration medium is generally the same as for leaf, except that the level of plant selection agent is preferably increased over time. Typically, the level will start out relatively low and be increased to the full desired sublethal level during the final portion of the regeneration culture. Such a step-wise approach allows transformed cells to multiply and gradually tolerate a higher level of the selected agent over time. For example, in the case of G418 as a plant selection agent, concentration of about 20 mg/l over the first week, 50 mg/l over the second week, and 75 mg/l over the third week in ITC medium may be used.

The shoots are first regenerated in the regeneration media as one or several shoot primordia, i.e., the beginnings of shoot structures. As the regeneration culture proceeds, the shoots multiply rapidly under controlled light conditions, typically about 16 hours/day at about 120–150 foot candles at a temperature of about 24° C. Within 6 to 7 weeks, 3 to 5 shoots per explant will typically be formed.

The particular regeneration protocols have also been found to be useful for shoot regeneration from non-transformed explant material. The regeneration medium will be generally as described above, except that the plant selection and the anti-Agrobacterium antibiotics will be removed. Regeneration frequencies may be obtained at a level of at least 20%, preferably at least 50%, and most preferably at least 80%, with frequencies up to 100% are possible (with frequency meaning the percent of explants producing shoots). It is possible to obtain an average of 15–20 regenerated shoots per explant within 6–8 weeks using this method. Use of the regeneration protocol has been found to produce up to about 10 to 15 shoots per explant over a 4 to 5 week period for leaf or a 7 to 8 week period for petal.

Optionally, the calli and shoot structures may be screened after about 2 to 3 weeks of the regeneration culture to identify transformants. When reporter genes, such as GUS or LUC have been introduced with the exogenous DNA sequences, screening may be conveniently performed by GUS assay (Jefferson (1986) PNAS USA 83:8447–8451) or LUC assay Ow, et al, *Science* (1986) 234:856–859. Transformed calli which are found to be chimeric, i.e., containing transformed and non-transformed cells, may be subjected to further screening on the plant selection agent. It has been found that additional selection and screening procedures result in the further production of transformed shoots.

Transformed shoots obtained from the regeneration medium will frequently be "vitrified." Such shoots are relatively short (usually from about 2 to 5 mm) and have leathery, thick, glossy leaves with a high water content. The leaves and stems of the vitrified shoots generally have a light green color and are often referred to as being glaucous or translucent.

Such vitrified shoots can be "normalized" by culturing in a normalizing medium for a period of weeks or months. The normalizing medium contains nutrients, an energy source, and a solidifying agent, but is generally free from growth regulators and hormones. Suitable nutrients and energy sources are generally as described for the general growth medium above. A preferred normalizing medium is MSO, as described in the Experimental section hereinafter, with about 1.2 to 1.8% TC agar.

The vitrified shoots are placed in the normalizing medium and new shoots are produced having normal morphology, i.e., narrow leaves, long cylindrical stems, with a dry and normal texture. The leaves have a dark green color. Culturing is carried out under about 16 hours/day light at about 120–150 foot candles, typically at about 24° C. After about 1 month, about 5 to 10% of the shoots will usually be normalized, while within 2 months, about 20 to 25% of the shoots will be normalized, while after 3 months, about 50 to 75% of the shoots will be normalized.

The shoots produced in the regeneration medium and optionally normalized will next be placed in a rooting medium which is generally the same as the general growth medium without the growth regulators and hormones. Gel-rite® is the preferred solidifying agent, usually being present at about 0.2 to 0.35%, preferably at about 0.25%. MSOG, as set forth in the Experimental section hereinafter, is a preferred rooting medium.

Shoots placed in the rooting medium will generally have roots initiated at their base after about 10 to 14 days in culture. The roots grow quickly and spread inside the rooting medium. The resulting plantlets may then be transferred to soil and are preferably kept in a high humidity environment by covering with plastic. More preferably, the shoots will be incubated in a growth chamber with 16 hours/light per day at about 25° C. during the day and 18° C. at night. After about 2 weeks during which time the plastic is gradually removed, the plants become hardened and may be subsequently transferred to greenhouse conditions. The plants thus produced are morphologically normal except for trait(s) which have been introduced by the exogenous DNA.

Optionally, the presence of a reporter gene may be assayed in the final plant material. The presence of the GUS gene or the LUC gene, e.g., may be assayed as described generally in Jefferson et al. (1986), supra., and Ow et al. (1980), supra. Other methods for determining the presence of the exogenous DNA fragments include restriction enzyme digestion, Southern blot hybridization, Northern blot hybridization, and polymerase chain reaction.

The present invention optionally employs a micropropagation step for multiplying the regenerated shoots, typically prior to normalization. After the shoots have been established in the regeneration medium, they may be separated and placed in fresh multiplication medium, typically containing nutrients, an energy source, an auxin, and a cytokinin (preferably including TDZ). The preferred media (preferably solid) include IT and BN as described in the Experimental section hereinafter. Such micropropagation can produce as many as 80 shoots per initial shoot which has cultured in the multiplication medium, typically within a period of about 6 to 8 weeks. Such micropropagation methods are suitable also optionally with a callus stage as described above, for non-transformed carnation shoots which may have been produced by other, conventional techniques.

The following examples are offered by way of illustration, not by way of limitation.

| EXPERIMENTAL MATERIALS | |
|---|---|
| Abbreviation/Name | Source/Reference |
| BA; Benzyl Adenine | Sigma Chemical Co., St. Louis, MO, USA |
| Carbenicillin (Geopen) | Roe RIG Pfizer, New York, NY, USA |
| 2,4-D; 2,4-Dichlorophenoxyacetic Acid | Sigma Chemical Co., St. Louis, MO, USA |
| NAA; Naphthalene Acetic Acid | Sigma Chemical Co., St. Louis, MO, USA |
| MS Salts | JRH Bioscience, Lexena, KS, USA |
| G148 (geneticin) | Sigma Chemical Co., St. Louis, MO, USA |
| B5 Vitamins | Gamborg et al. (1968) Exp. Cell. Res. 50:151–158 |
| MS Medium | Murashige and Skoog (1962) Physiol. Plant. 145:473–494 |
| MES; 2-N Morpholinoethane-sulfonic acid | Sigma Chemical Co., St. Louis, MO, USA |
| Acetosyringone | Aldrich Chemical Co., Milwaukee, WI, USA |
| Agar or TC Agar | Hazelton Biologics, Inc, Lexena, KS, USA |
| Gel-rite | Scott Lab. Inc., Warwick, RI, USA |
| Dropp, a cotton defoliant whose active ingredient is thidiazuron | Nor-Am Chemical Co., Wilmington, DE, USA |
| Kanamycin | Sigma Chemical Co., St. Louis, MO, USA |
| IBA; Indole Butyric Acid | Sigma Chemical Co., St. Louis, MO, USA |
| TDZ, Thidiazuron | Puri |
| MEDIA COMPOSITIONS | |
| MSC | |
| MS supplemented with Carbenicillin | 500 mg/l |
| MSO | |
| MS Salts | 1× |
| B5 vitamins | 1× |
| Sucrose | 30 g/l |
| MES | 0.59 g/l |

-continued

| | |
|---|---|
| Agar | 1.5% |
| pH | 5.8 |
| MSOG | |
| MS Salts | 1× |
| B5 Vitamins | 1× |
| Sucrose | 30 g/l |
| NES | 0.5 g/l |
| Gel-rite ® | 2.5 g/l |
| pH | 5.8 |
| BD | |
| MSOG medium supplemented with BA | 0.5 mg/l |
| 2,4-D | 0.5 mg/l |
| BDAS | |
| BD Supplemented with Acetosyringone | 100 μM |
| BDC | |
| BD supplemented with Carbenicillin | 500 mg/l |
| BDCK | |
| BD supplemented with Carbenicillin | 500 mg/l |
| Kanamycin | 200 mg/l |
| Min A | |
| KH$_2$PO$_4$ | 10.5 g/l |
| (NH$_4$)2SO$_4$ | 1.0 g/l |
| Sodium Citrite | 0.5 g/l |
| Agar | 15 g/l |
| BN | |
| Ms medium | 1× |
| BA | 1 mg/l |
| NAA | 0.02 mg/l |
| BNCK | |
| BN supplemented with Carbenicillin | 500 mg/l |
| Kanamycin | 200 mg/l |
| IT | |
| MSOG medium supplemented with IBA | 0.5 mg/l |
| TDZ | 0.165 mg/l |
| ITC | |
| IT supplemented with Carbenicillin | 500 mg/l |
| ITCK | |
| IT supplemented with Carbenicillin | 500 mg/l |
| Kanamycin | 200 mg/l |
| DT | |
| MSOG medium supplemented with 2,4-D | 0.5 mg/l |
| TDZ | 0.165 mg/l |
| DTC | |
| DT supplemented with Carbenicillin | 500 mg/l |
| DTAS | |
| DT supplemented with Acetosyringone | 100 μM |
| L-Broth* | |
| Tryptone | 10 g/l |
| Yeast Extract | 5 g/l |
| NaCl | 5 g/l |
| Glucose | 1 g/l |
| Agar | 15 g/l |

*pH adjusted to 7.0 to 7.2 using 0.1-5H NaOH before adding agar; dispense at 25 ml/plate.

PLASMIDS

The plasmid pJJ3499 contains DNA from the following sources:

1. *Escherichia coli* DNA in the pRK290 plasmid vector, the Tn5 neomycin phosphotransferase (NPT), and the β glucuronidase (GUS) gene.
2. *Agrobacterium tumefaciens* octopine strain DNA in the left and right border region and the polyadenylation site of the NPT and GUS genes.
3. *A. tumefaciens* nopaline strain DNA, with nopaline synthase DNA as the promoter of the NPT gene.
4. Cauliflower mosaic virus (CAMV) 35S promoter DNA directing expression of the GUS gene.

The plasmid pSLJ1911 is the same as above except that CAMV 35S promoter DNA directs expression of the NPT gene as well. The NPT gene was derived from the binary vector plasmid pJJ2964, which carries within the T-DNA region the unique sites BamHI and HindIII. Another plasmid based on a pUC replicon, pJJ3431, carries a 35S/GUS/ocs 3' fusion between a BglII site at the promoter end and a HindIII site at the 3' end. A BglII/HindIII fragment carrying this chimeric GUS gene was ligated to pJJ2964 DNA which had been cut with BamHI and HindIII. After transformation of the ligation, minipreps were carried out on individual colonies and a clone identified in which the GUS fusion had been ligated into the binary vector.

Plasmids pJJ3499 and pSLJ1911 were introduced into Agrobacterium using a triparental mating (Ditta et al. (1980), Proc. Nat. Acad. Sci. USA, 77:7347–7351).

METHODS RESULTS

EXAMPLE 1

Carnation transformation—Leaf bases (Improved White Sim). See Table 1.

1. Preparation of Source Tissues

Leaves were obtained from shoot cultures and prepared as follows:

(i) A shoot culture of Improved White Sim ("IWS") carnation (Yoder Bros., Barberton, Ohio, USA) was prepared starting from meristem tissue in the nodes and from meristem tissue in the shoot tips. Cuttings were made containing meristem tissue. The cuttings were surface sterilized in 75% ethanol for two minutes; then sterilized in 20% commercial bleach plus 0.1% Tween®-20 for 20 minutes; then rinsed three times in sterile distilled water. Under a dissection microscope, meristem tissues about 1–3 mm in size (diameter), were isolated.

(ii) The meristem tissues were pre-treated on BN medium with 1 mg/l BA (Sigma) and 0.02 mg/l NAA (Sigma). On this medium shoots were multiplied at high frequencies. Typically within 6–8 weeks 20–50 shoots were obtained from a single meristem cultured. From any one of these shoots 50–100 additional shoots were obtained within 6–8 weeks by subculturing every 4 weeks.

(iii) Some of the shoot cultures were subjected to a heat shock treatment at 40° C. for 4 hours in an incubator.

(iv) Leaves about 5–15 mm in size were then pulled from shoot cultures. Shoot primordia in the base of leaves were removed with a pair of forceps in order to eliminate the performed meristems, increase callus formation, and induce wound sites for Agrobacterium mediated transformation. Leaf or leaf base explants were subsequently cocultivated with Agrobacterium.

2. Agrobacterium and Culture Medium

Figure 1:
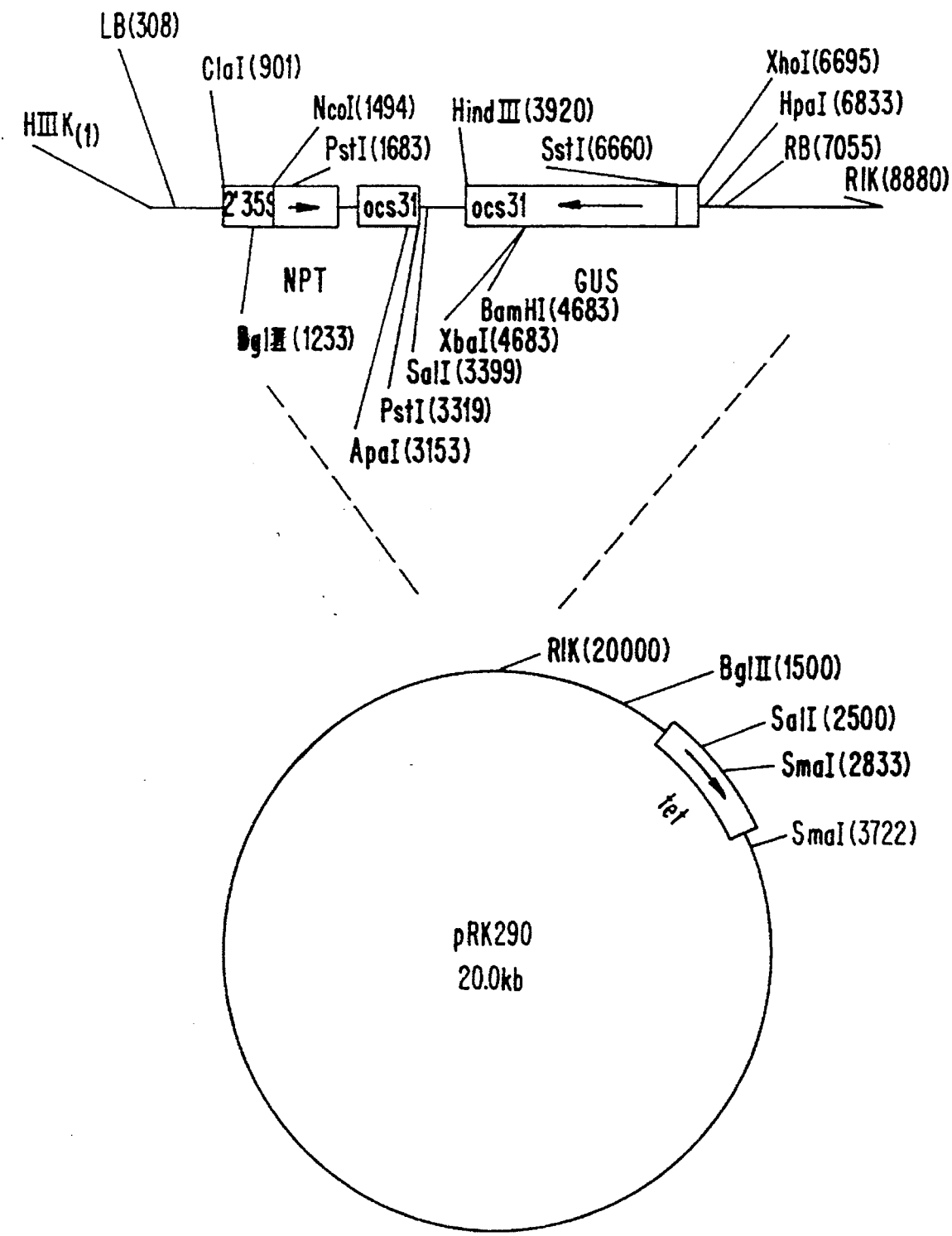
FIG. 1 is a map of plasmid pSLJ1911 employed in Examples 1 and 3. LB and RB are left and right borders of T-DNA respectively. Restriction enzyme sites are indicated, e.g. as HindIII, with a number which indicates the base number distance from HIIIK. On pRK290, the number adjacent to the restriction site denotes the distance from the RIK site.

*Agrobacterium tumefaciens* strain EHA101 (Hood et al. (1986) J. Bacteriology, 168:1291–1301, containing the binary vector pSLJ911 (FIG. 1) was cultured on L-Broth solid medium in plates containing 10 mg/l tetracycline for 2 days in dark at 28° C. At the end of this period, when the bacterial cultures were still white-cream in color (i.e., before browning), the cells were scraped off the medium and suspended in a 20 ml liquid medium ($10^9$ cells/ml). The medium was Induction Broth supplemented with 10mM nopaline. (Winnas et al. (1988) J. Bacteriology, 170:4047–4054. The bacterial suspension was shaken at 110 rpm for 3 hours before use.

3. Cocultivation on Cocultivation Medium to Yield Transformed Cells

BD medium containing acetosyringone (AS) at 100 μM concentration (BDAS medium) was used as cocultivation medium. Leaf explants were mixed with Agrobacterium suspension cells ($10^9$ cells/ml as prepared above). The Agrobacterium suspension was sufficient to cover all explants (around 20 ml for 200 explants). The mixture was shaken at 110 rpm, for 1 hour at 24° C. The mixture was then placed on a filter paper (Whatman #1), on the BDAS medium and excess liquid was removed. Leaf explants and Agrobacterium were cocultured (in 16 hour/day light) at 24° C. for 4 days. For controls, uninoculated tissues (prepared as in Step 1) were placed on BDAS medium.

4. Culture on Callus Initiation Medium to Yield Transformed Callus

After 4-day cocultivation, explants were transferred to callus initiation medium. This medium was BD medium supplemented with 500 mg/l carbenicillin/BDC medium) further supplemented with either 0, 35, or 50 mg/l G418 (plant selection marker). Callus initiation cultures were kept in a growth chamber (16 hour/day at 1200–1500 lux, 24°±1° C.) for 2 weeks. During this period, explants produced calli and shoots at their bases at different frequencies.

plied rapidly. Shoots were regenerated under 16 hour/day (1500 lux) light at 24° C. The regeneration rate was several shoots per explant. Within 6–7 weeks, 3–5 shoots per explant were regenerated. In the treatments without Agrobacterium inoculation, 10–15 shoots per explant were regenerated within 5 weeks.

6. Screening of Calli and Shoots for Transformation

Three weeks after Agrobacterium inoculation, calli and shoots were initially screened for transformants by GUS assay (Jefferson, (1986) PNAS, USA 83:8447–8451). Transformed calli were observed. Transformed calli were chimeric (a mixture of transformed and non-transformed cells) which were then subjected to further selection or screening. Materials which consisted of calli and shoot primordia were transferred to regeneration medium (see Part 5 of this Example) three weeks after cocultivation. After the second round three weeks after the first screen of selection/screening, two clusters of transformed shoots were obtained. Each cluster derived from a single explant.

7. Culture on Normalizing Medium to Yield Non-Vitrified Shoots

The regenerated shoots were observed to be vitrified. Shoots (1–2 cm) were cultured in MSO medium. Normal carnation shoots were produced. Culturing was carried out in Magenta GA-7 cubes (Magenta Corp. Chicago).

During culture new shoots were produced which had narrow leaves, long cylindrical stems, and with a dry and normal texture. Leaves had a dark green color. Normal shoots were thus produced. Culturing conditions of about 16 hour/day light (1500 lux) about 24° C. were used. Generally about 20% of the shoots were normalized within about one month.

8. Rooting Rooting Media

The rooting medium was MSOG. Normalized shoots (2–3 cm) were inserted 2–3mm into the medium.

Generally at the base of each stem, several roots were initiated after 14 days in culture. These roots grew very fast

TABLE 1

| | | IWS leaf base transformation with *Agrobacterium tumefaciens* EHA101 (pSLJ1911) | | | | | | |
|---|---|---|---|---|---|---|---|---|
| | | Selection | | % | GUS ASSAYS*** | | | |
| | | with G418 | No. | Explants | First screening | | Second screening | |
| Treatment | Heat Shock | (mg/l) | Explants | Survived | No. tested | % GUS+* | No. tested | % GUS+ |
| Inoculation | Yes | 0 | 30 | 97 | 8 | 0 | 0 | |
| with EHA101 | | 35 | 120 | 50 | 36 | 55 | 11 | 63** |
| (pSLJ1911) | | 50 | 130 | 46 | 44 | 77 | 13 | 85** |
| | No | 0 | 30 | 100 | 5 | 0 | 0 | |
| | | 35 | 85 | 48 | 22 | 36 | 4 | 25* |
| | | 50 | 80 | 45 | 18 | 44 | 6 | 25* |
| Uninoculated | Yes | 0 | 12 | 100 | 2 | 0 | | |
| Control | | 35 | 15 | 53 | 1 | 0 | | |
| | | 50 | 15 | 40 | 1 | 0 | | |
| | No | 0 | 15 | 100 | 1 | 0 | | |
| | | 35 | 15 | 47 | 1 | 0 | | |
| | | 50 | 15 | 47 | 1 | 0 | | |

*Samples having only dots or a patch of blue in the calli were GUS+; most of tissues within a "GUS+ sample" were negative for GUS staining.
**These samples resulted in production of transgenic plants. For the group of 11 tested, 3 were shoots. For the group of 13 tested, 2 were shoots. Of the 5 shoots, 2 were fully transformed (one from each group).
***These data are combined results for transformed calli and transformed shoots.

5. Culture on Regeneration Medium to Yield Regenerated Shoots

The regeneration medium was ITC supplemented with 75, 100, or 150 mg/l G418. Shoots were regenerated first as one or several shoot primordia. These were the beginning of shoot structures. During culture, shoots eventually multiand spread inside the rooting medium within a week. Plantlets were transferred to soil kept in a high humidity environment by covering with plastic and incubated in a growth chamber (16 hour light (16 hr/day 1200 lux) at 25° C. day, 18° C. night) for about two weeks. During this time the plastic was gradually removed and the plants were subsequently transferred to greenhouse conditions. The plants appeared normal morphologically and phenotypically.

9. Results

Figure 2:
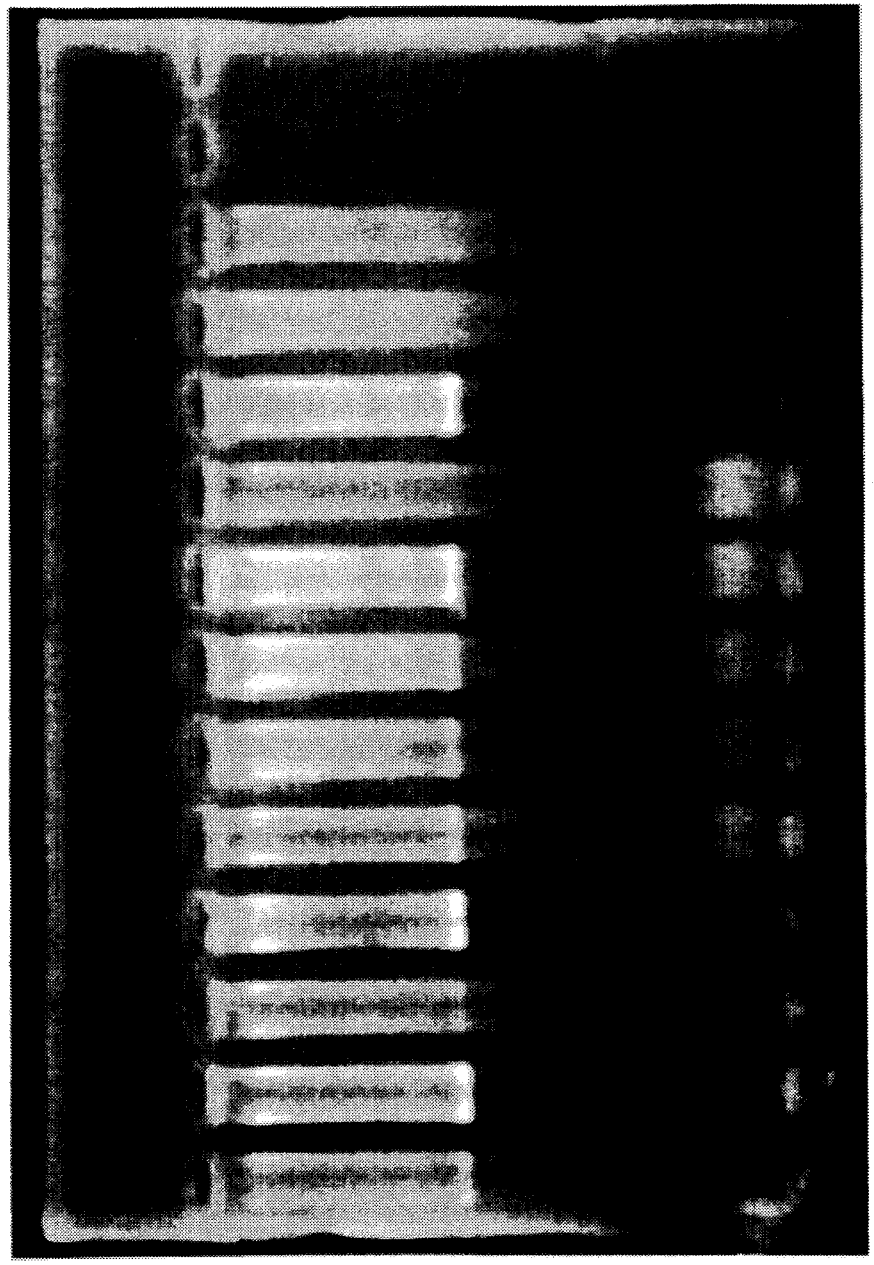
FIG. 2 is a gel showing the presence of introduced DNA amplified by PCR. The lanes are as follows.

Transformation was confirmed by growing or rooting in MSOG medium supplemented with 50 mg/l kanamycin. The presence of an introduced reporter gene was also tested in order to confirm transformation (Table 1) by GUS (β-glucuronidase) assays. (Jefferson et al., (1986) supra). The inserted DNA fragment was additionally detected using Polymerase Chain Reaction (PCR) technology (FIG. 2). The presence of a DNA band (shown by arrow in FIG. 2) indicates that the plant from which the sample was taken was transformed. All the GUS-positive plants were verified by PCR (Table 4).

EXAMPLE 2

Carnation transformation—Petal bases (Improved White Sim). See Table 2.

1. Preparation of Source Tissues

Flower buds of Improved White Sim ("IWS") carnation (Yoder Bros., Barberton, USA) not yet open were harvested from plants grown in greenhouses. The buds were about 2 cm long and were surface sterilized in 75% ethanol for 2 minutes; then sterilized in 20% commercial bleach for 20 minutes; and then rinsed three times in sterile distilled water. The basal portion of individual petals (about 5 mm in size) were isolated for culturing.

2. Agrobacterium and culture Medium

*Agrobacterium rhizogenes* 15834 (Birot, A. et al. (1987) *Plant Physiol. Biochem.* 25:323–325) was used for inoculation. These bacteria contained pJJ3499 plasmid (FIG. 3).

Agrobacterium cells were cultured on L-Broth medium containing tetracycline at 5 mg/l for 2 days in the dark at 28° C. At the end of this period, when the bacterial cultures were still whitish-creamish in color (i.e., before browning), the cells were scraped off the medium and suspended in Min A liquid medium ($10^9$ cells/ml) to be used for inoculation.

3. Cocultivation on Cocultivation Medium to Yield Transformed Cells

Petal bases were mixed with Agrobacterium, shaken at 110 rpm for 2 hrs, and plated for 2 days on a filter paper on a cocultivation medium. Also, control uninoculated tissues were prepared as step 1 above and plated on DTAS.

4. Culture on Callus Initiation Medium to Yield Transformed Callus

Petals were transferred to a callus induction medium consisting of DT medium supplemented with 500 mg/l carbenicillin (DTC medium) further supplemented with 0, 10, 15, and 25 mg/l G418 (plant selection agent. The culture process was carried out as in Example 1, Part 4. For regeneration efficiencies, see Table 2.

TABLE 2

| | IWS petal base transformation with *Agrobacterium rhizogenes* 15834 (pJJ3499) | | | | | | | |
|---|---|---|---|---|---|---|---|---|
| Treatment | 1st Step Selection, G418 (mg/l) | No. Explants | Survival Rate (%) | First GUS* (%+) | 2nd Step Selection G418 (mg/l) | Second GUS* (%+) | 3rd Step Selection, G418 (mg/l) | Third GUS (%+) |
| 15834 | 0 | 15 | 100 | 29 | 0 | 50 | 0 | 0 |
| | 10 | 60 | 80 | 100 | 25 | 30 | 50 | 25* |
| | 15 | 60 | 80 | 75 | 35 | 33 | 75 | 50** |
| | 25 | 60 | 67 | 83 | 50 | 35 | 100 | 24* |
| Uninoculated Control | 0 | 10 | 100 | 0 | | | | |
| | 10 | 10 | 80 | 0 | | | | |
| | 15 | 10 | 60 | 0 | | | | |
| | 25 | 10 | 60 | 0 | | | | |

*Refers to calli or shoots having dots or patches which were GUS+ (blue)
**These materials resulted in production of transgenic plants. For these samples, 18 were tested and, of these, 3 were shoots (the rest were calli). Of these three, one was a fully transformed shoot.

5. Culture on Regeneration Medium to Yield Regenerated Shoots

The regeneration medium was the same as for leaf (Example 1, Part 5) with the following modifications. Antibiotic concentrations were increased step-wise (Table 2). Tissues were on first-step selection for 25 days, on second-step selection for 15 days, and on third-step selection for 30 days or longer.

The culture process was the same as Example 1, Part 5 except that for the uninoculated petal bases, 10–15 shoots per explant were regenerated within 7–8 weeks.

6. Screen Calli and Shoot for Transformation

This step was carried out in the same way as Example 1, Part 6. See Table 2.

7. Culture on Normalizing Medium to Yield Non-Vitrified Shoots

This step was carried out in the same way as Example 1, Part 7. Shoots from petal bases generally were slightly more vitrified than from leaf bases. Therefore, it took 7–10 days longer for them to normalize.

8. Root in Rooting Medium

This step was carried out in the same way as Example 1, Part 8, and the resulting roots appeared similar to those reported in Example 1, Part 8.

9. Results

From 67–80% of inoculated explants survived the first-step selection, and 75–100% of these produced transformed chimeric calli (Table 2). By the 3rd GUS assay (done after application of 3rd-step selection), transformed shoots were identified (Tables 2 and 4). Uninoculated control explants did not produce GUS+ materials. Three of the transformants were tested and verified by PCR (FIG. 2).

EXAMPLE 3

Carnation Transformation—Leaf bases (Nathalie). See Table 3.

1. Preparation of Source Tissues

Leaves were obtained from shoot cultures of Nathalie carnation (obtained from Kooij Co., Holland) and prepared as in Example 1, except that 10–20 shoots were obtained from a single meristem cultured 6–8 weeks. From any one of these shoots, 30–40 additional shoots were obtained within 6–8 weeks by subculturing every 4 weeks.

2. Agrobacterium and Culture Medium

*Agrobacterium tumefaciens* EHA101 (pSLJ1911, FIG. 1) was used and prepared as in Example 1, part 2, except that Agrobacterium was suspended in Induction Broth.

3. Cocultivation on Cocultivation Medium to Yield Transformed Cells

The cocultivation medium was the same as for Example 1, Part 3, except that 0.1 mg/l 2,4-D was used in BDAS medium instead of 0.5 mg/l. The culture process was the same as in Example 1, Part 3. Controls for uninoculated explants were prepared as in Part 1 of this Example and plated on BDAS medium.

4. Culture on Callus Initiation Medium to Yield Transformed Callus or on Shoot Regeneration Medium to Yield Transformed Shoot The callus initiation medium was the same as for Example 1, Part 4, except that 0.1 mg/l 2,4-D was used in the BDC medium and the medium contained 0, 40, or 50 mg/l G418. Only one of the explants were plated on these media. The other one-half of explants were plated on regeneration medium immediately after cocultivation. This regeneration medium was the same as for Example 1, Part 5 (ITC) containing 0, 40, 50 mg/l G418. Control explants were treated similarly. The culture process was the same for Example 1, Part 4 except that both media produced calli and shoots at lower frequencies than for cultivar IWS (Table 3).

(Jefferson et al. (1986), supra.) Transformed calli and a transformed shoot were observed. Shoot transformation was confirmed by GUS$^+$. See Part 9 below Transformed calli were chimeric.

Transformed calli are subjected to further selection or screening. In the second and third round of selection or screening, additional transformed shoots result.

7. Culture on Normalizing Medium to Yield Non-Vitrified Shoots

Regenerated shoots may be vitrified. Therefore, shoots are cultured in MSO medium to produce normal carnation shoots. Culturing is carried out in Majenta GA-7 cubes (Majenta Corp. Chicago). During culture on normalizing medium, new shoots are produced which have narrow leaves, long cylindrical stems, and with a dry and normal texture. Leaves have a dark green color. Normal shoots are thus produced. Culturing is under 16 hour/day light (1500 lux) at about 24° C. Generally about 20–25 of the shoots were normalized within about 6 weeks.

8. Root in Rooting Medium

This step is carried out in the same way as for Example 1, Part 8 to yield plantlets.

9. Results

Transformation of the plantlets is confirmed using GUS (β-glucuronidase) assays (Jefferson et al. (1986), supra. Transformation is also confirmed by rooting assay (root formation of shoots in the presence of 50 mg/l kanamycin) and PCR.

TABLE 3

Nathalie leaf base transformation with *A. tumefaciens* EHA101 (pSLJ1911).

| Treatment | Medium with G418 (mg/l) | No. Explants | % Explants Regenerating Shoots | % Explants callused | GUS Assay No. Tested | % positive |
|---|---|---|---|---|---|---|
| Inoculation with | BDC | 23 | 30 | 78 | 5 | 0 |
| EHA101 (pSLJ1911) | BDCG40 | 145 | 18 | 11 | 8 | 13* |
| | BDCG50 | 129 | 18 | 18 | 9 | 0 |
| | ITC | 26 | 23 | 100 | 3 | 0 |
| | ITCG40 | 139 | 23 | 53 | 11 | 18 |
| | ITCG50 | 135 | 13 | 46 | 9 | 56 |
| Uninoculated Control | BDC | 15 | 40 | 66 | — | — |
| | BDCG40 | 12 | 25 | 50 | — | — |
| | BDCG50 | 12 | 25 | 50 | 2 | 0 |
| | ITC | 15 | 60 | 100 | 2 | 0 |
| | ITCG40 | 14 | 50 | 57 | — | — |
| | ITCG50 | 12 | 50 | 92 | — | — |

*This resulted in production of a transformed shoot.

5. Culture of Calli on Regeneration Medium to Yield Regenerated Shoots

This step was the same as for Example 1, Part 5, except that the concentration of G418 was increased to 75 or 100 mg/l. Small explants were transferred to ITC medium with 75 mg/l and large explants were transformed to ITC medium with 100 mg/l G418.

Shoots were regenerated first as one or a few shoot primordia. These were the beginning of shoot structures. During culture, shoots eventually multiplied. Shoots were regenerated under 16 hour/day light (1500 lux) at 24° C. The regeneration rate averaged 2 per explant. Within 6–7 weeks, 1–2 shoots per explant were regenerated. In uninoculated control regeneration without selection/transformation, 3–4 shoots for explant were regenerated within 4–5 weeks.

6. Screen Calli and Shoots for Transformation

Four weeks after cocultivation calli and shoots were selected and screened for transformants by GUS assay

TABLE 4

Assays for Transgenic Plants (Examples 1–3)

| | GUS | | PCR | |
|---|---|---|---|---|
| Example | No. Tested | No. Positive | No. Tested | No. Positive |
| 1 | 13 | 13 | 6 | 6 |
| 2 | 8 | 8 | 2 | 2 |
| 3 | 1 | 1 | — | — |

Although the foregoing invention has been described in detail for purposes of clarity of understanding, it will be obvious that certain modifications may be practiced within the scope of the appended claims.

What is claimed is:

1. A method for genetically transforming carnation plant material, said method comprising:

cocultivating carnation plant material with *Agrobacterium tumefaciens* or *rhizogenes* cells carrying an exogenous DNA sequence;

initiating callus formation in the plant material; and selecting transformed plant cells.

2. A method as in claim 1, further comprising:

regenerating transformed shoots from the transformed plant cells; and inducing root formation in the transformed shoots.

3. A method as in claim 1, wherein the Agrobacterium cells carry the exogenous DNA sequence on a plasmid within a transfer DNA (T-DNA) region.

4. A method as in claim 1, wherein the exogenous DNA sequence includes a selectable marker gene and transformed plant cells are selected by initiating callus formation in a callus initiation medium which inhibits the growth of plant cells which have not been transformed.

5. A method for producing genetically altered carnation plants, said method comprising:

(a) cocultivation of carnation plant material with *Agrobacterium tumefaciens* or *rhizogenes* cells carrying an exogenous DNA sequence including a selectable marker gene in a cocultivation medium containing nutrients, an energy source, and an induction compound under conditions which allow the Agrobacterium cells to infect the plant material and transfer the exogenous DNA to the carnation chromosomes, wherein the carnation plant material is leaf obtained from shoots grown in culture;

(b) culturing plant material from step (a) in a callus initiation medium containing nutrients, an energy source, an auxin, a cytokinin, an anti-Agrobacterium antibiotic, and a plant selection agent which inhibits callus and shoot formation from plant material which does not express the selectable marker gene to produce transformed callus material; and (c) culturing transformed callus material in a regeneration medium containing nutrients, an energy source, an auxin, a cytokinin, an anti-Agrobacterium antibiotic, and the plant selection agent, present in amounts effective to produce transformed shoots.

6. A method of claim 5, wherein the shoots of step (a) are grown from maristen tissue which has been cultured on a pretreatment medium consisting nutrients, and energy source, and auxin, and a cytokinin present in amounts effective to induce shot proliferation.

7. A method as in claim 6, wherein the shoots of step (a) are further cultured on a medium containing nutrients an energy source but being substantially free from growth regulators in order to enhance subsequent callus or shoot formulation.

8. A method as in claim 5, wherein the shoots of step (a) are subjected to an elevated temperature for a preselected time prior to removing the leaf, wherein the temperature and length of time are selected to enhance subsequent transformation efficiency.

9. A method as in claim 8, wherein the temperature is in the range from about 35° to 45° C. and the time is in the range from about 2 to 8 hours.

10. A method as in claim 5, wherein shoot primordia are removed from the shoots of step (a) to produce the leaf prior to step (b).

11. A method as in claim 5, wherein the carnation plant material is petal obtained from rooted plants.

12. A method as in claim 1, wherein the transformed plant cells are transformed calli.

13. A method as in claim 5, wherein the Agrobacterium is *Agrobacterium tumefaciens*.

14. A method as in claim 5, wherein the Agrobacterium cells are present in the cocultivation medium at least about $10^7$ cells/ml.

15. A method as in claim 5, wherein the plant material and Agrobacterium cells in step (a) are first combined in a liquid culture for at least about 1 hour and then transferred to a solid phase matrix for at least about 2 days.

16. A method as in claim 5, wherein the plant material in step (b) is cultured for at least about 1 week in the callus initiation medium.

17. A method as in claim 5, wherein the concentration of plant selection agent in the callus initiation medium is selected to inhibit proliferation but permit survival of non-transformed plant material, whereby tranformed cells survive and proliferate at high levels.

18. A method as in claim 5, wherein the callus material is maintained in the regeneration medium for a time sufficient to produce at least about 3 shoots per callus.

19. A method as in claim 5, wherein the plant material is petal and the concentration of the plant selection agent in the regeneration medium is increased from an initially low level to a higher level as the tolerance of the transformed plant material increases.

20. A method as in claim 5, further comprising:

(d) rooting the shoots from step (c) in a rooting medium to produce transformed plantlets that may be planted in soil.

21. A method as in claim 20, further comprising:

culturing transformed shoots from step (c) prior to rooting in a normalizing medium containing nutrients and an energy source but being substantially free from growth regulators, whereby new shoots are produced which are free from vitrification.

22. A method for micropropagating shoots from transformed carnation plant material, said method comprising:

(a) culturing transformed carnation plant material obtained from callus to produce a plurality of vitrified shoots; and (b) placing vitrified shoots from step (a) in a medium containing nutrients and an energy source but being substantially free from growth regulators for a period of at least about one month, whereby new shoots are produced which are free from vitrification.

23. A method as in claim 22, wherein the medium further contains agar.

24. Carnation callus material derived from an explant material which has been transformed with an exogenous DNA sequence, wherein said DNA sequence comprises a functional gene capable of imparting a phenotype not possessed by the explant material and wherein said DNA sequence has been integrated into the carnation genome.

25. Carnation callus material derived from and explant material which has been transformed with the exogenous DNA sequence by the method of claim 1, wherein the DNA Sequence comprises a functional gene capable of imparting a phenotype not possessed by the explant material.

26. A carnation plant having cells derived from an explant material which have been transformed with an exogenous DNA sequence, wherein said DNA sequence comprises a functional gene capable of imparting a phenotype not possessed by the explant material and wherein said DNA sequence has been integrated into the carnation genome.

27. A carnation plant derived from an explant material which has been transformed with an exogenous DNA sequence by the method of claim 2, wherein the DNA sequence comprises a functional gene capable of imparting a phenotype not possessed by the explant material.

28. A carnation plant having cells derived from an explant material which have been transformed with an exogenous DNA sequence so that flowers of the plant display a phenotype characterized by controlled senescence resulting in prolonged vase life relative to the vase life of flowers from plants propagated from non-transformed cells of the explant material.

29. A transgenic carnation plant derived from an explant material comprising an exogenous DNA sequence so that flowers of the plant display a phenotype characterized by controlled senescence resulting in prolonged vase life relative to the vase life of flowers from plants propagated from non-transformed cells of the explant material.

30. A carnation plant as in claim 28 or 29, wherein the DNA sequence comprises an Acc synthase gene.

31. A carnation plant having cells derived from an explant material which have been transformed with an exogenous DNA sequence to display a phenotype characterized by resistance to a herbicide.

32. A transgenic carnation plant derived from an explant material comprising an exogenous DNA sequence to display a phenotype characterized by resistance to a herbicide.

33. A carnation plant as in claim 31 or 32, wherein the DNA sequence comprises a chlorsulfuron resistance gene.

34. A carnation plant having cells derived from an explant material which have been transformed with an exogenous DNA sequence so that flowers of the plant display a phenotype characterized by a color conferred by said exogenous DNA sequence which color is modified relative to a flower color of the explant material.

35. A transgenic carnation plant derived from an explant material comprising an exogenous DNA sequence so that flowers of the plant display a phenotype characterized by a modified color conferred by said exogenous DNA sequence which color is modified relative to a flower color of the explant material.

36. A carnation plant as in claim 34 or 35, wherein the DNA sequence comprises an Hf1 gene.

37. A carnation plant derived from an explant material having cells which have been transformed with an exogenous DNA sequence to display a phenotype characterized by enhanced resistance to disease relative to the disease resistance of plants propagated from non-transformed cells of the explant material.

38. A transgenic carnation plant derived from an explant material comprising an exogenous DNA sequence to display a phenotype characterized by enhanced resistance to disease relative to the disease resistance of plants propagated from non-transformed cells of the explant material.

39. Cut flowers from the carnation plants of any of claims 26, 27, 28, 29, 31, 32, 34, 37 or 38.

40. A carnation plant having cells which have been transformed with the ACC synthase gene.

41. A carnation plant having cells which have been transformed with a chlorsulfuron resistance gene.

* * * * *